(12) United States Patent
Liou

(10) Patent No.: US 7,097,161 B2
(45) Date of Patent: Aug. 29, 2006

(54) ELECTRICAL AIR FRESHENER DEVICE

(76) Inventor: Chii Moon Liou, P.O. Box 10-69, Chong Ho, Taipei (TW) 235

( * ) Notice: Subject to any disclaimer, the term of this patent is extended or adjusted under 35 U.S.C. 154(b) by 109 days.

(21) Appl. No.: 10/846,815

(22) Filed: May 14, 2004

(65) Prior Publication Data

US 2005/0253289 A1 Nov. 17, 2005

(51) Int. Cl.
*B01F 3/04* (2006.01)

(52) U.S. Cl. .................. 261/30; 261/142; 261/DIG. 88; 261/DIG. 89; 392/390; 455/90.1; 455/556.1; 455/575.1

(58) Field of Classification Search .................. 261/26, 261/30, 104, DIG. 88, DIG. 89, 142; 422/124; 455/90.1, 556.1, 575.1; 392/390, 392
See application file for complete search history.

(56) References Cited

U.S. PATENT DOCUMENTS

| 5,407,642 | A | | 4/1995 | Lord ........................... 422/122 |
| 5,887,118 | A | * | 3/1999 | Huffman et al. ............ 392/390 |
| 6,080,367 | A | | 6/2000 | Lin .............................. 422/124 |
| 6,850,697 | B1 | * | 2/2005 | Basaganas Millan ....... 392/390 |
| 2004/0204043 | A1 | * | 10/2004 | Wang et al. ............. 455/556.1 |

* cited by examiner

*Primary Examiner*—Robert A. Hopkins

(57) ABSTRACT

An air freshener device includes a card member for plugging to electric facility, a housing attached to the card member, a casing received in the housing to receive air freshener material, and a heater received in the housing for being energized to heat an air received in the housing when the card member is plugged to the electric facility, and to allow the air freshener material to flow out of the casing and to be heated by the heater. The card member includes a tubular member to receive the heater or the casing, and to anchor the housing to the tubular member. The housing includes a screen to show a quantity of the air freshener material.

10 Claims, 4 Drawing Sheets

ELECTRICAL AIR FRESHENER DEVICE

BACKGROUND OF THE INVENTION

1. Field of the Invention

The present invention relates to an air freshener device, and more particularly to a portable and electrical air freshener device for plugging or attaching to various electric facilities.

2. Description of the Prior Art

Various kinds of typical air freshener devices have been developed and well known in the art, and have typically been employed in such environments as a motor vehicle, the home, the office environment, and even in industry.

People may typically concern about exhaust, road smells, and even tobacco smoke in a motor vehicle, and may often concern with cooking odors, pet smells, or a general mustiness that can result from the house being sealed during inclement weather in the home.

The typical air freshener devices normally comprise an air freshening material disposed or contained therein, which will take the form of a solid, liquid, or gel, with a liquid typically being absorbed in a sponge or foam material.

The most typical air freshener devices normally comprise an air freshening material, a deodorant or deodorizer disposed or contained within a container which is closed by gluing, bonding, etc. However, the typical air freshening material to be suitably circulated within the motor vehicle, the home, the office, or the like.

For allowing the typical air freshening material to be suitably circulated within the motor vehicle, the home, the office, or the like, a clip mount may be attached to the typical air freshening device, for attaching or securing the typical air freshening device to a grill of a ventilator, or the like.

For example, U.S. Pat. No. 5,407,642 to Lord discloses one of the typical air freshening devices which includes a clip mount for attaching or securing the typical air freshening device to the grill of the ventilator, or the like, and for allowing an air stream issued from the ventilator to flow over the exposed surface of the air freshening material. Without the air stream issued from the ventilator, the air freshening material may not be suitably circulated within the motor vehicle, the home, the office, or the like.

U.S. Pat. No. 6,080,367 to Lin discloses another typical air freshening device which includes a fan device attached or secured to the typical air freshening device, to generate an air stream to flow over the exposed surface of the air freshening material and thus to circulate the air freshening material.

However, the fan device includes a large volume that may not be easily carried with the users, and the fan device is required to be plugged to the electric power suppliers of the vehicle or of the home, or of the office, or the like, and may not be plugged or coupled to various electric facilities.

The present invention has arisen to mitigate and/or obviate the afore-described disadvantages of the conventional air freshener devices.

SUMMARY OF THE INVENTION

The primary objective of the present invention is to provide an air freshener device that is portable and that may be easily carried with the users.

The other objective of the present invention is to provide an air freshener device for plugging or attaching to various electric facilities.

In accordance with one aspect of the invention, there is provided an air freshener device comprising a card member for plugging to electric facility, a housing attached to the card member, and including a hole formed therein, a casing received in the hole of the housing, to receive air freshener material therein, and a heater received in the hole of the housing, for being energized to heat an air received in the hole of the housing, when the card member is plugged to the electric facility, and to allow the air freshener material to flow out of the casing and to be heated by the heater.

The housing includes at least one air passage formed therein and communicating with the hole thereof, to allow air to circulate into and out of the housing. The housing includes a screen to show a quantity of the air freshener material.

The housing includes at least one projection extended into the hole thereof, and the heater includes at least one cavity formed therein to receive the projection of the housing, and to anchor the heater within the housing.

The card member includes a tubular member extended therefrom, the heater is extendible out of the housing, and extendible into the tubular member, to anchor the housing to the tubular member. An actuator may further be provided and engageable into and attachable to the tubular member.

The actuator is engageable with the heater, to disengage the heater from the tubular member. The tubular member includes a depression formed therein, the actuator includes a catch engageable into the depression of the tubular member, to secure the actuator to the tubular member.

A rod may further be provided and engaged between the casing and the heater. The casing includes an aperture formed therein to receive one end of the rod. The heater includes an orifice formed therein to receive one end of the rod. A spring may further be provided and engaged between the casing and the heater.

The card member includes a tubular member extended therefrom, the casing is extendible out of the housing, and extendible into the tubular member, to anchor the housing to the tubular member.

The tubular member includes a bore formed therein to receive the casing, and includes at least one jut extended into the bore thereof, and the casing includes at least one notch formed therein to receive the jut of the tubular member, and to anchor the casing within the tubular member and the housing.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
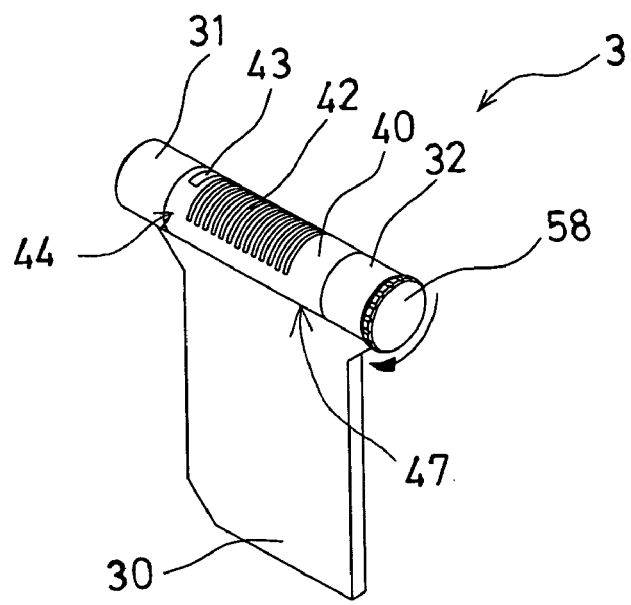
FIG. 1 is a perspective view of an air freshener device in accordance with the present invention.
Figure 2:
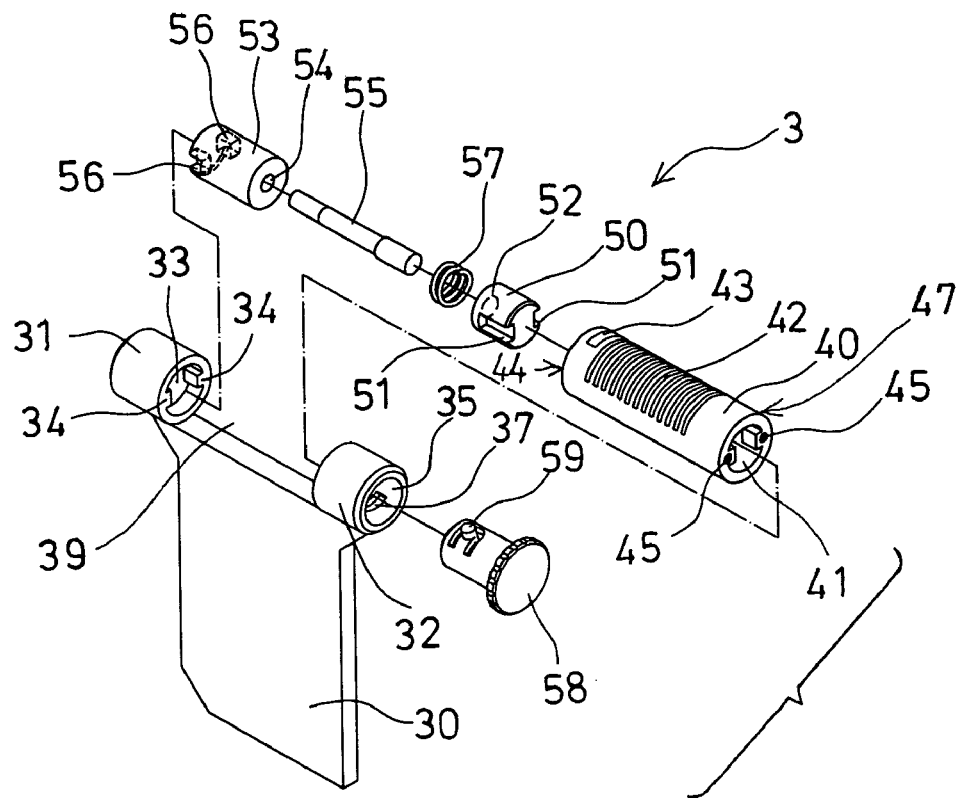
FIG. 2 is an exploded view of the air freshener device.
Figure 3:
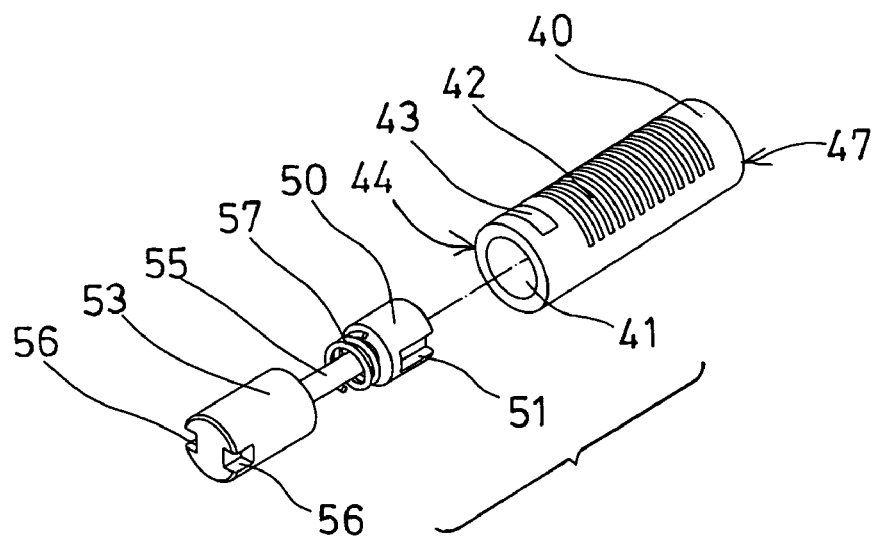
FIGS. 3, 4, 5 are partial exploded views illustrating the assembling operation of the air freshener device.

Referring to the drawings, and initially to FIGS. 1–3, an air freshener device 3 in accordance with the present invention comprises a card member 30 for plugging or coupling to an electric or computer device 1, such as for plugging to a slot or a coupler 13 of the electric or computer device 1, such as a portable phone or a mobile phone 10 (FIG. 6), a personal digital assistant (PDA) 11 (FIG. 7), or a personal computer or a note book computer 12 (FIG. 8), etc.

Figure 4:
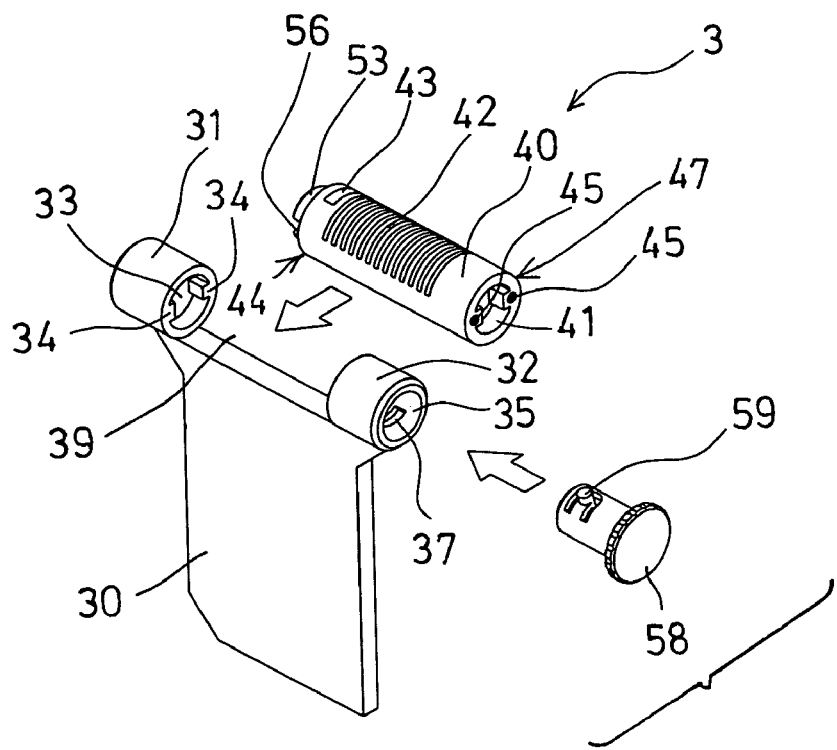

The freshener device 3 further includes one or more, such as two tubular members 31, 32 disposed or provided or extended from the card member 30, and preferably aligned with each other, and spaced away from each other, to form a space 39 between the tubular members 31, 32 (FIGS. 2, 4).

One of the tubular members 31 includes a bore 33 formed therein, and one or more juts 34 extended into the bore 33 thereof. The other tubular member 32 also includes a bore 35 formed therein, and a depression 37 formed therein and communicating with the bore 35 thereof.

The freshener device 3 further includes a housing 40, such as a tubular housing 40 to be disposed and anchored between the tubular members 31, 32. The housing 40 includes a hole 41 formed therein, and a number of air passages 42 formed therein and communicating with the hole 41 thereof, for allowing air to circulate into and out of the hole 41 of the housing 40.

The housing 40 includes a screen or a display 43 formed or provided on the outer portion thereof, and disposed close to one end 44 thereof, for displaying or showing the quantity of air freshener material (which will be discussed hereinafter), and includes one or more projections 45 extended into the hole 41 at the other end 47 thereof.

A heater 50 is engaged and received in the other end 47 of the housing 40, and includes one or more cavities 51 formed therein to receive the projections 45 of the housing 40, and to anchor and to position the heater 50 within the housing 40. The heater 50 includes an orifice 52 formed therein and facing away from the projections 45 of the housing 40, or facing toward the one end 44 of the housing 40.

It is preferable that the cavities 51 of the heater 50 include a depth or a length greater than the length of the projections 45 of the housing 40, for allowing the heater 50 to be slightly extended out of housing 40, and to be slightly extended into the tubular member 32, to anchor or secure the housing 40 to the tubular member 32.

A casing 53 is provided to receive the air freshener material therein, such as deodorant, deodorizer, perfume, environment fragrance, or the like, and in the form of a solid, liquid, or gel, with a liquid typically being absorbed in a sponge or foam material. The quantity of the air freshening material may be displayed or shown in the screen or display 43 of the housing 40.

The casing 53 includes an aperture 54 formed therein and facing toward the projections 45 of the housing 40, or facing away from the one end 44 of the housing 40. A rod 55 includes two ends engageable into the aperture 54 of the casing 53 and into the orifice 52 of the heater 50 respectively. The casing 53 includes one or more notches 56 formed therein to receive the juts 34 of the tubular member 31, and thus to anchor and to position the casing 53 to the tubular member 31.

It is to be noted that the casing 53 may be engaged in the tubular member 31 and the one end 44 of the housing 40, to latch or secure or anchor the housing 40 to the tubular member 31. In addition, the heater 50 may be engaged in the other end 47 of the housing 40 and may be extended into the tubular member 32, to latch or secure or anchor the housing 40 to the tubular member 32.

A spring 57 may be engaged onto the rod 55 and/or engaged between the heater 50 and the casing 53, to bias the casing 53 into the one end 44 of the housing 40, and to bias the heater 50 into the tubular member 32, such that the housing 40 may be stably latched or secured or anchored between the tubular members 31, 32.

Figure 5:
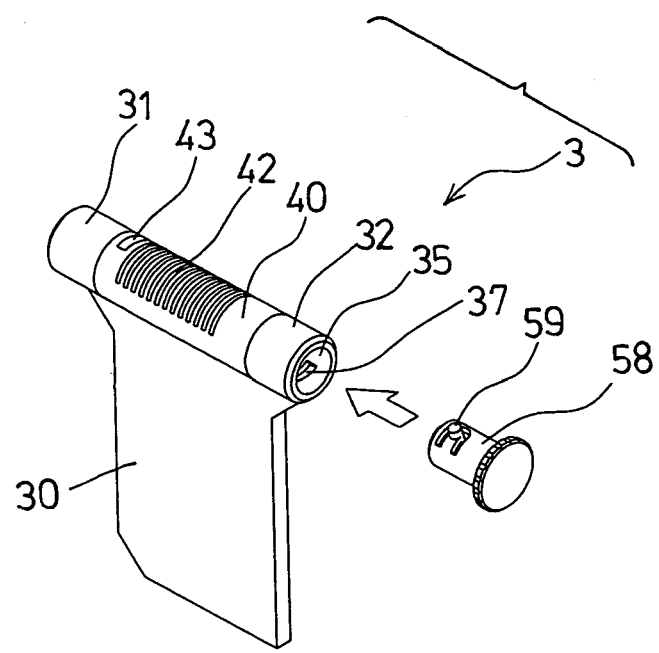

As shown in FIGS. 4 and 5, an actuator 58 is engageable into the bore 35 of the tubular member 32, and includes a spring biased catch 59 engageable into the depression 37 of the tubular member 32, to secure or lock the actuator 58 to the tubular member 32, and disengageable from the depression 37 of the tubular member 32 by rotating the actuator 58 relative to the tubular member 32, for allowing the actuator 58 to be detachably secured to the tubular member 32.

The actuator 58 is engageable with the heater 50, to move or force the heater 50 into the other end 47 of the housing 40, and to disengage the heater 50 from the tubular member 32, for allowing the other end 47 of the housing 40 to be moved relative to the tubular member 32, and to be disengaged from the tubular members 31, 32.

However, it is to be noted that, when the actuator 58 is secured to the tubular member 32, the housing 40 may still be anchored to the tubular member 31 by the casing 53, and the housing 40 will not be disengaged from the tubular members 31, 32, unless the other end 47 of the housing 40 to be moved laterally relative to the tubular member 32 by the users.

Figure 6:
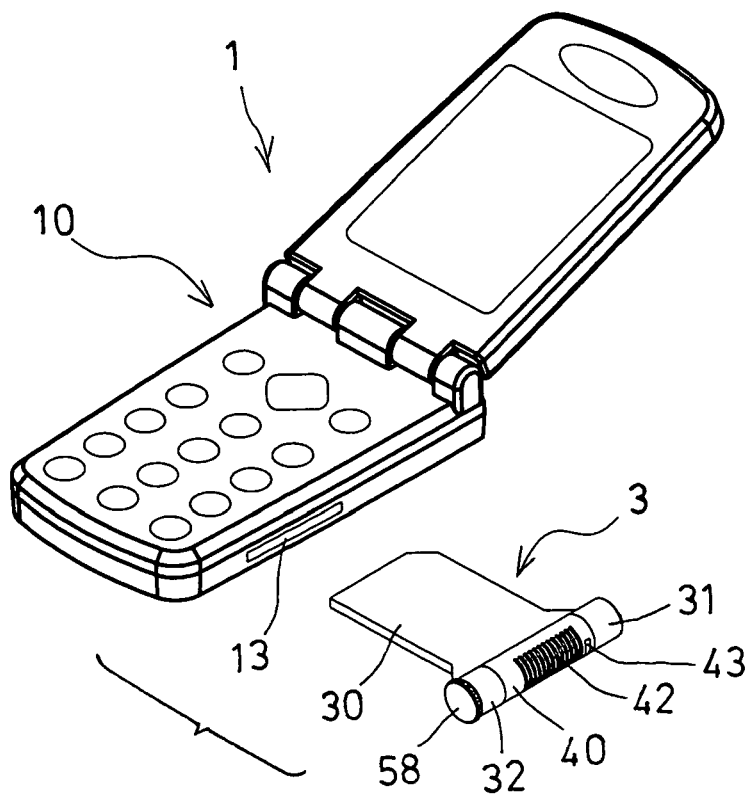
FIG. 6 is an exploded view illustrating the attachment of the air freshener device to a portable phone or a mobile phone.
Figure 7:
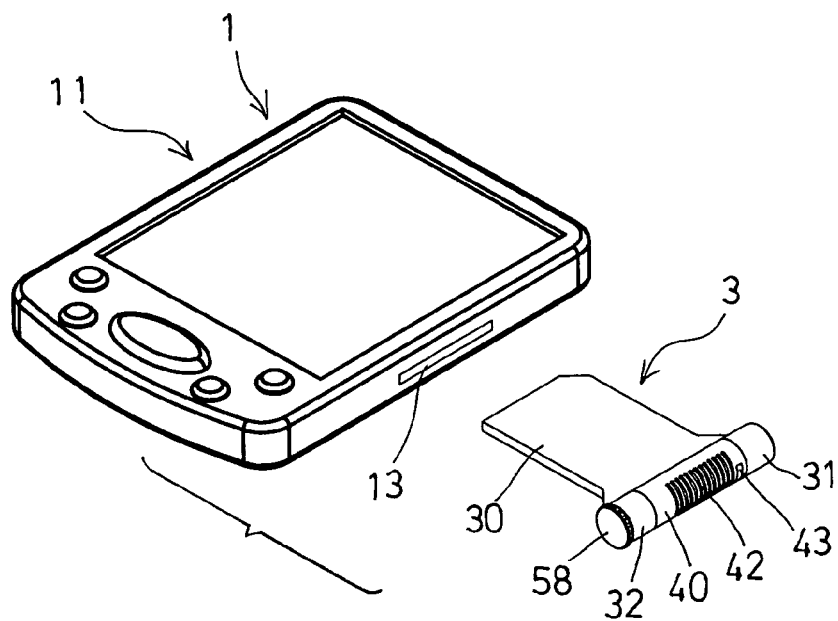
FIG. 7 is an exploded view similar to FIG. 6, illustrating the attachment of the air freshener device to a personal digital assistant.
Figure 8:
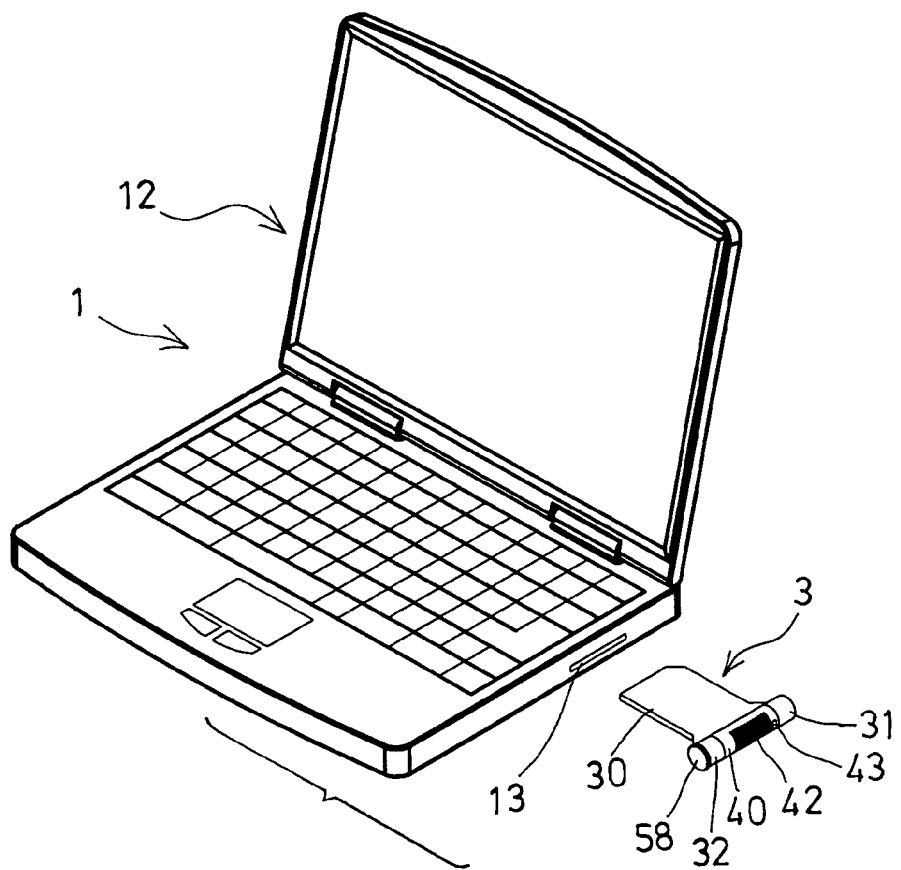
FIG. 8 is an exploded view similar to FIGS. 6 and 7, illustrating the attachment of the air freshener device to a personal computer or a note book computer.

In operation, as shown in FIGS. 6–8, the card member 30 of the air freshener device 3 may be plugged or coupled to either of the electric or computer devices 1, such as the portable phone or mobile phone 10 (FIG. 6), the personal digital assistant (PDA) 11 (FIG. 7), or the personal computer or note book computer 12 (FIG. 8), etc., for allowing the heater 50 to be energized by the electric power sources of the electric or computer devices 1.

It is to be noted that the coupling of the card member 30 to the electric power sources of the electric or computer devices 1 is typical, and the energizing of the card member 30 by the electric power sources of the electric or computer devices 1 is also typical, such that the heater 50 may also be coupled to and energized by the electric power sources of the electric or computer devices 1.

When the heater 50 is energized, the air received in the housing 40 may be heated by the heater 50 and may then flow out or circulate out through the air passages 42 of the housing 40, such that the pressure within the housing 40 will be decreased. The air freshener material received in the casing 53 may then be drawn or flown or permeate out through the aperture 54 of the casing 53, or through a gap formed between the rod 55 and the casing 53, due to the decreased pressure within the housing 40.

The air freshener material drawn or flown or permeate out through the aperture 54 of the casing 53, or through the gap formed between the rod 55 and the casing 53 may then be heated by the heater 50 and may then flow out or circulate out through the air passages 42 of the housing 40, to freshen the environment or the like.

The quantity of the air freshener material may be seen through the screen or display 43 of the housing 40, for allowing the users to unplug the card member 30 of the air freshener device 3 from the electric or computer devices 1 when the housing 40 has no air freshener material received or contained therein.

It is to be noted that the air freshener device in accordance with the present invention includes a compact structure that may be easily carried with the users, and that may be easily plugged or attached to various electric facilities, such as computer devices. The typical air freshener devices have no card member for plugging or attaching to various electric facilities.

Accordingly, the air freshener device in accordance with the present invention includes a portable structure for being easily carried with the users, and for plugging or attaching to various electric facilities.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. An air freshener device comprising:
a card member for plugging to an electric or computer device, a housing attached to said card member, and including a hole formed therein, a casing received in said hole of said housing, to receive air freshener material therein, and a heater received in said hole of said housing, for being energized to heat an air received in said hole of said housing, when said card member is plugged to the electric or computer device, and to allow the air freshener material to flow out of said casing and to be heated by said heater; and
wherein said housing includes a screen to show a quantity of the air freshener material.

2. The air freshener device as claimed in claim 1, wherein said housing includes at least one projection extended into said hole thereof, and said heater includes at least one cavity formed therein to receive said at least one projection of said housing, and to anchor said heater within said housing.

3. The air freshener device as claimed in claim 1, wherein said card member includes a tubular member extended therefrom, said heater is extendible out of said housing, and extendible into said tubular member, to anchor said housing to said tubular member.

4. The air freshener device as claimed in claim 3 further comprising an actuator engageable into and attachable to said tubular member.

5. The air freshener device as claimed in claim 4, wherein said actuator is engageable with said heater, to disengage said heater from said tubular member.

6. The air freshener device as claimed in claim 4, wherein said tubular member includes a depression formed therein, said actuator includes a catch engageable into said depression of said tubular member, to secure said actuator to said tubular member.

7. The air freshener device as claimed in claim 1, further comprising a rod engaged between said casing and said heater.

8. The air freshener device as claimed in claim 1, further comprising a spring engaged between said casing and said heater.

9. The air freshener device as claimed in claim 1, wherein said card member includes a tubular member extended therefrom, said casing is extendible out of said housing, and extendible into said tubular member, to anchor said housing to said tubular member.

10. The air freshener device as claimed in claim 9, wherein said tubular member includes a bore formed therein to receive said casing, and includes at least one jut extended into said bore thereof, and said casing includes at least one notch formed therein to receive said at least one jut of said tubular member, and to anchor said casing within said tubular member and said housing.

* * * * *